United States Patent [19]

DesJardin et al.

[11] Patent Number: 4,782,161

[45] Date of Patent: Nov. 1, 1988

[54] PREPARATION OF FLUOROPYRIDINES

[75] Inventors: Michael A. DesJardin, San Ramon, Calif.; Craig B. Murchison, Midland, Mich.

[73] Assignee: The Dow Chemical Company, Midland, Mich.

[21] Appl. No.: 111,375

[22] Filed: Oct. 21, 1987

[51] Int. Cl.$^4$ .............. C07D 213/57; C07D 213/26; C07D 213/02

[52] U.S. Cl. .................... 546/345; 546/287; 546/346

[58] Field of Search .............. 546/345, 287

[56] References Cited

U.S. PATENT DOCUMENTS

| | | | |
|---|---|---|---|
| 3,978,000 | 8/1976 | Schmitt, Jr. et al. | 546/345 |
| 4,029,600 | 6/1977 | Schmitt, Jr. et al. | 546/345 |
| 4,547,577 | 10/1985 | Gatlin et al. | 546/345 |
| 4,563,530 | 1/1986 | Fujioka et al. | 546/345 |
| 4,680,406 | 7/1987 | Fujioka, Jr. et al. | 546/345 |

OTHER PUBLICATIONS

Carson et al., Chem. Abs., vol. 77, 126439h, 1970.
Diprose et al., Chem. Abs., vol. 73, 1970, 98802t.
Chem. Abs., vol. 94, 1981, 94:47146h.

*Primary Examiner*—Alan L. Rotman
*Assistant Examiner*—Robert C. Whittenbaugh
*Attorney, Agent, or Firm*—D. Wendell Osborne

[57] ABSTRACT

Fluoropyridine compounds, including 3- and 5-fluoropyridines, are prepared in an improved process by contacting chloropyridine compounds with hydrogen fluoride in the vapor phase in the presence of an activated carbon catalyst having large diameter pores. Thus, 2,3-difluoro-5-(trifluoromethyl)pyridine is prepared by contacting 3-chloro-2-fluoro-5-(trifluoromethyl)pyridine with excess hydrogen fluoride at about 500° C. in the presence of an activated carbon catalyst having an average pore diameter of about 100 Angstroms.

15 Claims, No Drawings

PREPARATION OF FLUOROPYRIDINES

BACKGROUND OF INVENTION

The present invention relates to an improved process for preparing pyridine compounds substituted with fluorine.

Pyridine compounds possessing fluoro substituents are useful intermediates in the preparation of biologically active compounds, including herbicides, plant growth regulators, insecticides, and fungicides. The compound 2,3-difluoro-5-(trifluoromethyl)pyridine, for example, is useful in the preparation of the herbicide 2-(4-((3-fluoro-5-(trifluoromethyl)-2-pyridinyl)oxy)-phenoxy)propanoic acid. In a like manner, the compound 3,5-dichloro-2,4,6-trifluoropyridine is useful in the preparation of the herbicide 4-amino-3,5-dichloro-6-fluoro-2-pyridinyloxyacetic acid.

Current processes for the preparation of pyridine compounds possessing fluoro substituents, while functional, often produce large amounts of waste products, are inefficient, or are otherwise costly. This is particularly true with respect to 3- and 5-fluoropyridine compounds. One of the simpler methods known, which involves the replacement of chloro substituents with fluoro substituents by treating with hydrogen fluoride at an elevated temperature in the presence of an activated charcoal catalyst, is disclosed in U.S. Pat. No. 4,563,530. The process described therein, however, suffers from a relatively slow reaction rate and from a relatively rapid rate of deactivation of the catalysts employed.

SUMMARY OF THE INVENTION

It has now been found that activated carbon catalysts having average pore diameters of greater than about 60 Angstroms surprisingly are much more catalytic (more effective in increasing the reaction rate) and much more resistant to deactivation than are activated carbon catalysts having smaller average pore diameters in the reaction of hydrogen fluoride with chloropyridines to obtain fluoropyridines at elevated temperatures.

The present invention encompasses the process for preparing a fluoropyridine compound of the formula

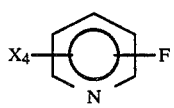

FORMULA I wherein
each X independently represents H, $CF_3$, $CHF_2$, Cl, F, CN, or $CH_3$, with the proviso that no more than three of X represent H or $CH_3$
which method comprises contacting a chloropyridine of the formula

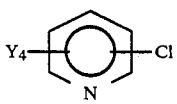

FORMULA II wherein
each Y independently represents H, $CF_3$, $CHF_2$, $CCl_3$, $CHCl_2$, Cl, F, CN, or $CH_3$, with the proviso that no more than three of Y represent H or $CH_3$
with hydrogen fluoride at about 350° C. to about 650° C. in the presence of a thermostable, activated carbon catalyst having an average pore diameter of greater than about 60 Angstroms under conditions conducive to fluoride exchange and replacing at least one Cl substituent with F.

In a particularly preferred embodiment of the present invention, 2,3-difluoro-5-(trifluoromethyl)pyridine is prepared by contacting 3-chloro-2-fluoro-5-(trifluoromethyl) pyridine with hydrogen fluoride at about 400° C. to about 600° C. in the presence of a thermostable, activated carbon catalyst having an average pore diameter of greater than about 80 Angstroms. Wide pore carbon catalysts produced by American Cyanamid and described in U.S. Pat. No. 3,978,000 are especially preferred.

The products of the process can be recovered, if desired, by conventional methods and further purified, if desired, by conventional methods to obtain useful intermediates.

DETAILED DESCRIPTION OF THE INVENTION

The products of the present invention are characterized by having at least one fluoro substituent and are defined by Formula I wherein each of the four X moieties independently represents H, $CF_3$, $CHF_2$, Cl, F, CN, or $CH_3$, with the proviso that at least three represent substituents other than H or $CH_3$, i.e., are electron withdrawing. Compounds of Formula I wherein at least one X moiety represents $CF_3$, Cl, or F are preferred. The compound 2,3-difluoro-5-(trifluoromethyl)pyridine is more preferred.

The chloropyridine starting materials of the present invention are similar to the products except that they are characterized by having at least one chloro substituent which is converted to a fluoro substituent in the process. They are illustrated by Formula II wherein each of the four Y moieties independently represent H, $CF_3$, $CCl_3$, $CHCl_2$, Cl, F, CN, or $CH_3$ with the proviso that at least three represent substituents other than H or $CH_3$; i.e., an electron withdrawing substituent. Compounds of Formula II wherein at least one Y moiety represents $CF_3$, Cl, or F are preferred. The compound 3-chloro-2-fluoro-5- (trifluoromethyl)pyridine is more preferred.

When chloropyridines of Formula II wherein one or more Y moieties represent $CCl_3$ or $CHCl_2$ are employed, these moieties, are generally converted to $CF_3$ and $CHF_2$ moieties, respectively, in the process. Thus, for example, 2,3-dichloro-5-(trichloromethyl)pyridine produces as a major product 2-fluoro-3-chloro-5-(trifluoromethyl)-pyridine.

When chloropyridines of Formula II wherein one or more Y moieties represent chloro are employed, some of the chloro substituents in addition to the —Cl moiety of Formula II may be replaced by fluoro. Generally, chloro substituents in the 2-, 4-, and 6-positions react preferentially to chloro substituents in the 3- and 5-positions. The replacement of more than one chloro substituent by fluoro in a chloropyridine of Formula II in the process is within the definition of this invention and is an important aspect of the invention. Thus, for example, 3,5-dichoro-2,4,6-trifluoropyridine is made in the process from pentachloropyridine. In this situation, the overall process can be viewed as a series of reactions as described herein taking place consecutively in the same process. Thus, in the example, the reaction can be viewed (ignoring the isomeric products that form) as a compound of Formula II wherein the —Cl is in the 2-position and $Y_4$ represents 3,4,5,6-tetrachloro being converted in a first reaction to a compound of Formula I wherein the —F is in the 2 position and $Y_4$ represents 3,4,5,6-tetrachloro, which compound is also a compound of Formula II wherein —Cl is in the 6-position and $Y_4$ represents 2-fluoro-3,4,5-trichloro. This compound is then converted in a second reaction into a compound of Formula I wherein the —F is in the 6-position and $Y_4$ represents 2-fluoro-3,4,5-trichloro, which compound is also a compound of Formula II wherein —Cl is in the 4-position and $Y_4$ represents 3,5-dichloro-2,6-difluoro. This compound is then converted in a third reaction into a compound of Formula I wherein the —F is in the 4-position and $Y_4$ represents 3,5-dichloro-2,6-difluoro. In the example the last named product is the major recovered product. By a proper choice of reaction conditions, using the guidelines given herein, any of the named intermediates can be made to be a major product. In addition, two further reaction steps analogous to those described can be realized and pentafluoropyridine recovered as a major product.

The replacement of 3- and 5-position chloro substituents by fluoro is an especially valuable aspect of the invention as this transformation is, in general, difficult to achieve.

The starting materials of Formula II are for the most part known in the art. All others can be prepared by methods described in the art for related compounds. The preparation of the more preferred starting material, 3-chloro-2-fluoro-5-(trifluoromethyl)pyridine, is described in U.S. Pat. No. 4,547,577.

Hydrogen fluoride in a substantially anhydrous form as used in the process is commercially available. It is employed in at least about an equimolar amount with respect to the chloropyridine reactant of Formula II. Generally molar ratios of about 1 to about 20 are employed. Ratios of about 2 to about 16 are preferred and those of about 3 to about 12 are more preferred.

The thermostable, activated carbon catalysts of the present invention have an average pore diameter of at least 60 and generally less than about 400 Angstroms. Average pore diameters of greater than 70 and less than about 300 Angstroms are preferred and those greater than about 80 and less than about 200 Angstroms are more preferred. One specificially preferred wide pore carbon has an average pore diameter of about 100 Angstroms and has about 97 percent mesoporosity. The cylindrical pore model was used for pore diameter determinations.

Activated carbon catalysts having surface areas of about 100 m²/g to about 1000 m²/g are generally suitable and those having surface areas of about 200 m²/g to about 800 m²/g are preferred. One specifically preferred catalyst has a surface area of about 340 m²/g.

The activated carbon catalysts of the present invention can be in any of the common forms suitable for passing organic vapors through. Granular or pelletized prills are generally more convenient than powdered forms for most situations, but powdered forms may be used, for example, in fluidized bed reactors. One specifically preferred catalyst is in the form of extruded cylinders 0.64 cm in diameter and 1 to 1.5 cm. in length.

Suitable activated carbon catalysts are available. Some appropriate types of carbon are described in U.S. Pat. Nos. 3,978,000 and 4,029,600.

The rate of reaction in the process is dependent upon the amount of catalyst present. Sufficient catalyst is generally employed so that the conversion that takes place under the reaction conditions and in the reactor employed results in recoverable product. Generally, in a continuous reactor about 5 g to about 50 kg of catalyst are employed for every mole of chloropyridine passed through the reactor per hour. About 50 g to about 5 kg of catalyst per mole of chloropyridine per hour are preferred.

The activated carbon catalyst is advantageously dried and preconditioned before use. This can be accomplished in conventional ways, such as by heating the catalyst, usually in the reactor to be used for the process of the invention, and passing first an inert gas, such as nitrogen, and then hydrogen fluoride gas through the reactor. Temperatures of about 350° C. to about 550° C. are typically employed for this procedure.

Any reactor suitable for vapor phase reactions in the presence of solid catalysts can be used in the process. Packed tube, fixed-basket constantly stirred tank, and fluidized bed reactors are typical. Continuous type reactors are preferred.

The process is generally conducted in the manner described in U.S. Pat. No. 4,563,530, all teachings of which are, hereby, incorporated by reference. In a typical procedure, the reactor is first charged with a large pore carbon catalyst as defined herein. The reactor is then heated to the desired reaction temperature and the catalyst is typically dried and preconditioned. A chloropyridine compound of Formula II and hydrogen fluoride are heated, either separately or as a mixture, in order to vaporize them and to aid in controlling the temperature in the reactor. The hot gaseous reactants are then introduced into the reactor, either individually or as a mixture, and allowed to contact the catalyst. The reaction product mixture formed by contacting the starting materials with the catalyst under conditions conducive to the formation of fluoropyridine compounds of Formula I is allowed to exit the reactor and is recovered. Recovery usually takes the form of condensation, but other methods such as trapping, quenching, or absorption can be employed. Condensation is typically accomplished by passing the reaction product mixture through one or more cooled vessels. It is possible and usual to achieve some separation of the unreacted hydrogen fluoride and by-product hydrogen chloride from the compounds of Formulas I and II in the mixture by adjusting the temperature and other conditions of condensation. The reaction mixture recovered can be used as is or the desired products of Formula I can be further purified before use as intermediates. Standard methods of purification can be employed; distillative methods are preferred. Unreacted or partially reacted chloropyridine starting materials and unreacted hydrogen fluoride that are recovered as components of the reaction product mixture can be recycled in the process.

Conditions conducive to fluoride exchange vary somewhat depending upon parameters such as the specific starting chloropyridine of Formula II, the specific catalyst, the amount of catalyst and the mole ratio of hydrogen fluoride to chloropyridine employed. In general, temperatures of about 350° C. to about 650° C. are suitable. Temperatures of about 400° C. to about 600° C. are preferred, and temperatures of about 450° C. to about 550° C. are more preferred. Pressures of about 0.5 atmosphere to about 50 atmospheres are suitable. Pressures of about 1 atmosphere to about 5 atmospheres are preferred. It is often convenient to operate at pressures reflecting the total of atmospheric pressure and the normal back pressure of the reactor. Contact times of about 2 seconds to about 120 seconds are common. Contact times about 5 to about 80 seconds are preferred and of about 10 to about 60 seconds are more preferred. Using the teachings of this application and the precepts of chemical kinetics, one of average skill in the art can readily determine suitable conditions for the preparation of each compound represented by Formula I.

The following examples are presented to illustrate the invention and should not be construed as limiting the claims.

EXAMPLE 1

A 3 in. Hastalloy C Berty reactor manufactured by Autoclave Engineering, Inc., Erie, Pa., which is a high internal recyle vapor phase reactor, was employed. This reactor has a 3 in. diameter upright cylindrical cavity into which is fitted a centrally located, upright cylindrical catalyst basket having wire retainer screen ends and which is surrounded by a cylindrical draft tube. An impeller powered by a magnetic drive, which is used to create turbulence in the reactor and to circulate the reaction mixture up and through the catalyst basket, is mounted in the bottom portion of the cavity. The reactor was fitted with electrically heated inlet and outlet ports, both located near the bottom of the reactor below the impeller, with a pressure gauge, and with thermocouples mounted near the top and near the bottom. The reactor was heated with a three zone electrical heating jacket around the body and a band heater around the head and was insulated to minimize heat loss.

An evaporator consisting of a 0.25 in. nickel pipe in a 0.50 in. nickel sleeve surrounded by ceramic resistive superheaters was attached to the inlet port by a heated 0.25 in. nickel tube. Two methylene chloride/dry ice cooled condensers and a caustic scrubber column were attached in series to the outlet port by a heated 0.25 in. nickel tube. A by-pass vapor condensor was also attached in parallel. The impeller shaft seal was fitted with a jacket and the resulting cavity filled with nitrogen under positive pressure to prevent vapor escape.

The catalyst basket was loaded with 36.7 g of the specifically preferred activated carbon described herein. The reactor was heated to about 500° C. with the impeller rotating at about 1500 rpm and the catalyst was dried and conditioned by passing 30 ml of hydrogen fluoride through the reactor over about 30 minutes (this appeared from the results to be a less than an optimum amount of conditioning). Conditioning was omitted in successive runs. A mixture containing a ratio of 1 mole of 3-chloro-2-fluoro-5-(trifluoromethyl)pyridine to 3.8 moles of hydrogen fluoride was prepared and fed to the evaporator, which was heated at the desired temperature, at the rate of about 0.36 g per min and the hot volatilized reactants were allowed to flow into the hot reactor at the same rate. This produced an effective residence time of about 12-15 seconds. The organic materials and some of the inorganic acids exiting the reactor through the reactor outlet port were condensed in the cold traps and some of the inorganic acids (HF and HCL) were neutralized in the caustic scrubber. The contents of the cold traps were diluted with carbon tetrachloride, neutralized with sodium bicarbonate, dried over magnesium sulfate, and filtered. The filter cake was rinsed with more carbon tetrachloride and all of the organics were combined before analysis. An internal standard gas chromatographic analysis using a capillary columm coated with DB 225 was employed and tetrachlorobenzene and/or 3,5-dichloropyridine was used as the standard. The results of four runs made after two initial shake-down runs are given in the following table:

| Run | Temp., °C.[1] | Residence Time, sec. | Feed Rate, g/min. | GC Analysis of Effluent, normalized mole percent[4] | |
|---|---|---|---|---|---|
| | | | | Reactant[2] | Product[3] |
| A | 508 | 14.5 | 0.35 | 84.7 | 15.3 |
| B | 515 | 14.2 | 0.36 | 83.5 | 16.5 |
| C | 517 | 11.7 | 0.38 | 82.8 | 17.2 |
| D | 553 | 12.2 | 0.34 | 82.7 | 17.3 |

[1]Average of the two thermocouples (top and bottom)
[2]3-Chloro-2-fluoro-5-(trifluoromethyl)pyridine
[3]2,3-Difluoro-5-(trifluoromethyl)pyridine
[4]Small amounts of 2-fluoro-5-(trifluoromethyl)pyridine and several unknowns were present as well.

Average of the two thermocouples (top and bottom) 3-Chloro-2-fluoro-5-(trifluoromethyl)pyridine 2,3-Difluoro-5-(trifluoromethyl)pyridine. Small amounts of 2-fluoro-5-(trifluoromethyl)pyridine and several unknowns were present as well.

EXAMPLE 2

The reactor, reactants, catalyst conditions, and procedures of Example 1 were employed except that the amount of catalyst used was varied. The catalyst was conditioned at about 500° C. by carrying out and discarding an initial run; there was no additional conditioning between runs. The results of 11 runs are given in the following table:

| Run | Temp., °C.[1] | Catalyst, g | Feed Rate, g/min | Analysis of Effluent[5] | | | |
|---|---|---|---|---|---|---|---|
| | | | | Reactant[2] | Product[3] | By-product[4] | Unidentified Products |
| E | 514 | 40.5 | 0.34 | 79.6 | 16.0 | 4.4 | 6.1 |
| F | 513 | 40.5 | 0.35 | 77.4 | 17.7 | 4.8 | 10.0 |
| G | 516 | 40.5 | 0.36 | 83.7 | 13.2 | 3.9 | 5.4 |
| H | 392 | 40.5 | 0.36 | 88.9 | 9.1 | 2.0 | 1.4 |
| I | 515 | 40.5 | 0.37 | 77.1 | 18.4 | 4.5 | 10.9 |
| J | 541 | 40.5 | 0.37 | 78.4 | 16.8 | 4.8 | 16.0 |
| K | 516 | 40.5 | 0.36 | 77.5 | 18.7 | 3.9 | 10.0 |
| L | 517 | 13.5 | 0.36 | 84.5 | 12.7 | 2.8 | 4.7 |
| M | 517 | 13.5 | 0.36 | 85.5 | 12.0 | 2.5 | 4.0 |
| N | 519 | 27.0 | 0.36 | 77.9 | 19.3 | 2.8 | 7.3 |
| O | 519 | 27.0 | 0.36 | 79.5 | 17.8 | 2.7 | 6.5 |

[1]Average of two thermocouples (top and bottom)
[2]3-Chloro-2-fluoro-5-(trifluoromethyl)pyridine
[3]2,3-Difluoro-5-(trifluoromethyl)pyridine
[4]2-Fluoro-5-(trifluoromethyl)pyridine (about 1.5 percent 2-chloro-5-(trifluoromethyl)pyridine in reactant)
[5]Reactant, Product, and By-product values are normalized mole percent; Unidentified Products values are area percent of all peaks.

Average of two thermocouples (top and bottom) 3-Chloro-2-fluoro-5-(trifluoromethyl)pyridine 2,3-Difluoro-5-(trifluoromethyl)pyridine 2-Fluoro-5-(trifluoromethyl)pyridine (about 1.5 percent 2-chloro-5-(trifluoromethyl)pyridine in reactant). Reactant, Product, and By-product values are normalized mole percent; Unidentified Products values are area percent of all peaks.

We claim:

1. A process for preparing a fluoropyridine compound of the formula

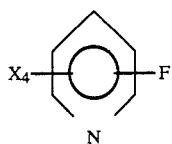

wherein
each X independently represents H, CF$_3$, CHF$_2$, Cl, F, CN, or CH$_3$, with the proviso that no more than three of X represent H or CH$_3$
which comprises contacting a chloropyridine compound of the formula

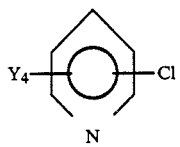

wherein
each Y dependently represents H, CF$_3$, CHF$_2$, CCl$_3$, CHCl$_2$, Cl, F, CN, or CH$_3$, with the proviso that no more than three of Y represent H or CH$_3$
with hydrogen fluoride at about 350° C. to about 650° C. in the presence of a thermostable, activated carbon catalyst having an average pore diameter of greater than about 60 Angstroms, under conditions conducive to fluoride exchange, and replacing at least one Cl substituent with F.

2. A process according to claim 1 wherein the fluoropyridine compound prepared is additionally recovered.

3. A process according to claim 1 wherein the temperature is about 400° C. to about 600° C.

4. A process according to claim 1 wherein the process is conducted in a continuous manner.

5. A process according to claim 1 wherein the catalyst has an average pore diameter of about 80 to about 200 Angstroms.

6. A process according to claim 5 wherein the catalyst has an average pore diameter of about 100 Angstroms and a surface area of about 340 m$^2$/g and is in the form of extruded cylinders.

7. A process according to claim 1 wherein at least one of Y$_4$ represents CF$_3$, Cl, or F.

8. A process according to claim 7 wherein at least one of Y$_4$ represents CF$_3$.

9. A process according to claim 7 wherein at least one of Y$_4$ represents Cl or F.

10. A process according to claim 7 wherein the chloropyridine compound is 3-chloro-2-fluoro-5-(trifluoromethyl)pyridine and the fluoropyridine compound prepared is 2,3-difluoro-5-(trifluoromethyl)pyridine.

11. A process according to claim 10 wherein the fluoropyridine compound prepared is additionally recovered.

12. A process according to claim 10 wherein the temperature is about 400° C. to about 600° C.

13. A process according to claim 10 wherein the process is conducted in a continuous manner.

14. A process according to claim 10 wherein the catalyst has an average pore diameter of about 80 to about 200 Angstroms.

15. A process according to claim 14 wherein the catalyst has an average pore diameter of about 100 Angstroms and a surface area of about 340 m$^2$/g and is in the form of extruded cylinders.

* * * * *

UNITED STATES PATENT AND TRADEMARK OFFICE
CERTIFICATE OF CORRECTION

PATENT NO. : 4,782,161

DATED : November 1, 1988

INVENTOR(S) : Michael A. DesJardin; Craig B. Murchison

It is certified that error appears in the above-identified patent and that said Letters Patent is hereby corrected as shown below:

Col. 1, line 67, delete "$CHC_{12}$" and insert -- $CHCl_2$ --;

Col. 2, line 40, delete "$CC_{13}$" and insert -- $CCl_3$ --;

Col. 3, line 47, "specifically" has been misspelled;

Col. 4, lines 30-31, delete "chloropyidine" and insert -- chloropyridine --;

Col. 5, line 19, delete "recyle" and insert -- recycle --;

Col. 5, line 22, "catalyst" has been misspelled;

Col. 5, line 23, delete "cylindical" and insert -- cylindrical --;

Col. 5, line 65, delete "HCL" and insert -- HCl --;

Col. 6, delete lines 23-27 and lines 58-65;

UNITED STATES PATENT AND TRADEMARK OFFICE
CERTIFICATE OF CORRECTION

PATENT NO. : 4,782,161

DATED : November 1, 1988            Page 2 of 2

INVENTOR(S) : Michael A. DesJardin; Craig B. Murchison

It is certified that error appears in the above-identified patent and that said Letters Patent is hereby corrected as shown below:

Col. 7, line 25, delete "dependently" and insert -- independently --.

Signed and Sealed this

Eighteenth Day of July, 1989

Attest:

DONALD J. QUIGG

Attesting Officer      Commissioner of Patents and Trademarks